(12) United States Patent
Masada et al.

(10) Patent No.: US 8,333,188 B2
(45) Date of Patent: Dec. 18, 2012

(54) MEDICINE EJECTION APPARATUS AND CONTROL METHOD THEREOF

(75) Inventors: Yohei Masada, Kawasaki (JP); Mitsuru Imai, Chichibu (JP); Keisuke Kawahara, Tokyo (JP); Masahiro Takei, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 154 days.

(21) Appl. No.: 12/532,867

(22) PCT Filed: Jan. 23, 2009

(86) PCT No.: PCT/JP2009/051515
§ 371 (c)(1),
(2), (4) Date: Sep. 24, 2009

(87) PCT Pub. No.: WO2009/093759
PCT Pub. Date: Jul. 30, 2009

(65) Prior Publication Data
US 2010/0275916 A1  Nov. 4, 2010

(30) Foreign Application Priority Data

Jan. 25, 2008 (JP) ................... 2008-014458
Apr. 11, 2008 (JP) ................... 2008-103554

(51) Int. Cl.
*A61M 11/00* (2006.01)
*A61M 16/00* (2006.01)
*A61M 15/00* (2006.01)
*A62B 7/00* (2006.01)
*A62B 9/00* (2006.01)

(52) U.S. Cl. ......... 128/200.22; 128/200.14; 128/200.24; 128/203.12; 128/203.15; 128/202.22; 128/205.23

(58) Field of Classification Search ............ 128/200.11–200.23, 200.24, 203.12, 203.15, 202.17; 239/357, 326, 349, 354; 222/187, 383.1, 222/634
See application file for complete search history.

(56) References Cited

U.S. PATENT DOCUMENTS
5,363,842 A * 11/1994 Mishelevich et al. .... 128/200.14
(Continued)

FOREIGN PATENT DOCUMENTS
CA          2165961          8/2005
(Continued)

OTHER PUBLICATIONS

Office Action dated Nov. 15, 2011, issued in counterpart Chinese Patent Application No. 200980102596.3, with translation.
(Continued)

*Primary Examiner* — Annette Dixon
(74) *Attorney, Agent, or Firm* — Fitzpatrick, Cella, Harper & Scinto

(57) ABSTRACT

A medicine ejection apparatus which ejects a medicine for medicating a user has a medicine ejecting unit, which has an element that generates energy for ejecting the medicine, a drive control unit which controls a drive start and a drive stop of the element, and an ejection amount determining unit, which determines a total amount of a medicine that is ejected from the medicine ejecting unit after the element performs a drive stop. The drive control unit enables the element to perform driving to eject an amount of medicine calculated from a difference between a set ejection amount and the total amount of medicine that has actually been ejected, when the total amount ejected, as determined by the ejection amount determining unit, is less than the set ejection amount.

9 Claims, 13 Drawing Sheets

U.S. PATENT DOCUMENTS

| | | | |
|---|---|---|---|
| 5,435,282 A * | 7/1995 | Haber et al. | 128/200.16 |
| 5,509,404 A | 4/1996 | Lloyd et al. | 128/200.14 |
| 5,515,842 A * | 5/1996 | Ramseyer et al. | 128/200.18 |
| 7,513,253 B2 | 4/2009 | Kobayashi et al. | 128/203.21 |
| 7,896,006 B2 * | 3/2011 | Hamano et al. | 128/204.15 |
| 2002/0187248 A1 | 12/2002 | Childers | 427/2.1 |
| 2007/0017512 A1* | 1/2007 | Peter et al. | 128/203.15 |
| 2007/0062520 A1 | 3/2007 | Nobutani et al. | 128/200.14 |
| 2007/0125370 A1 | 6/2007 | Denyer et al. | 128/200.14 |
| 2007/0227534 A1 | 10/2007 | Nobutani et al. | 128/200.14 |
| 2007/0240712 A1 | 10/2007 | Fleming et al. | 128/203.15 |

FOREIGN PATENT DOCUMENTS

| | | |
|---|---|---|
| CN | 1788806 | 6/2006 |
| CN | 2905088 | 5/2007 |
| EP | 1452199 | 9/2004 |
| EP | 1882488 | 1/2008 |
| JP | H10-507096 | 7/1998 |
| JP | 2003-024442 A | 1/2003 |
| JP | 2004249208 A | 9/2004 |
| JP | 2004-283245 | 10/2004 |
| JP | 2006-506151 | 2/2006 |
| JP | 2006198127 A | 8/2006 |

OTHER PUBLICATIONS

Japanese Office Action dated Aug. 28, 2012 issued in the counterpart application No. 2008-103554, along with its English-language translation (6 pages).

* cited by examiner

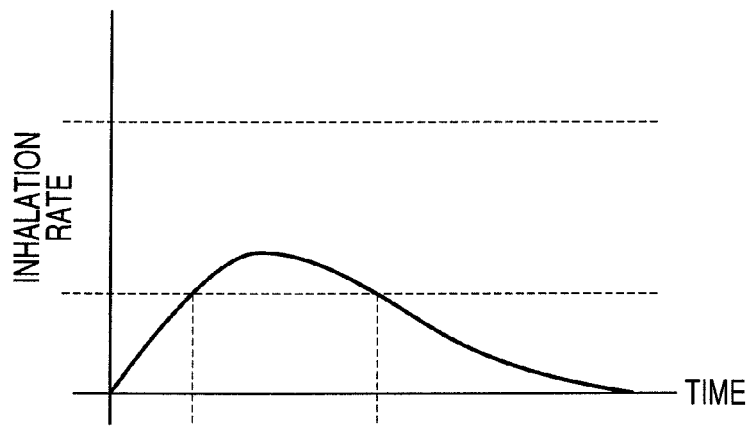
FIG. 3A
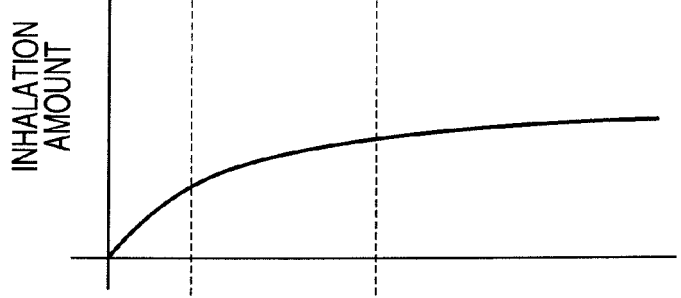
FIG. 3B
FIG. 3C
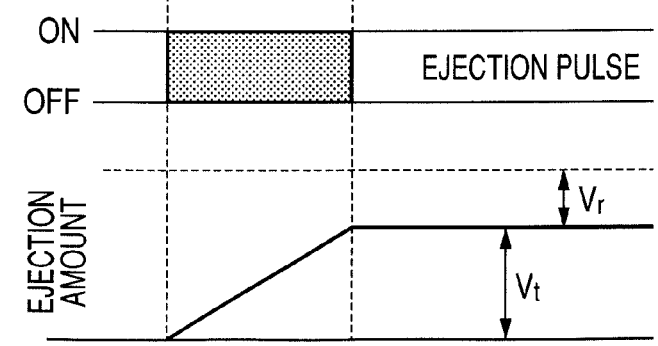
FIG. 3D

FIG. 4A
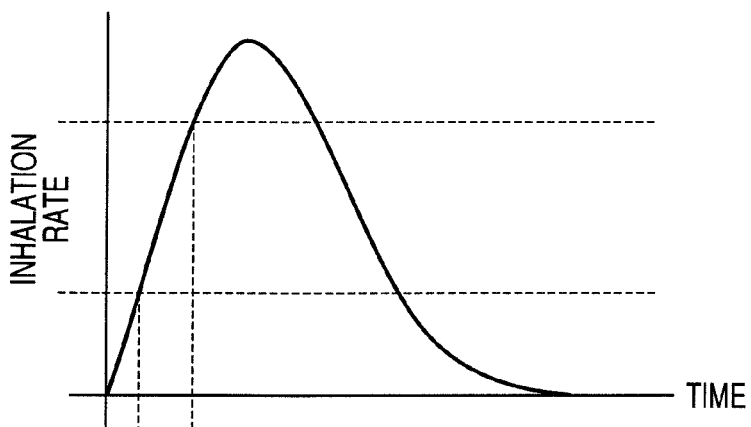
FIG. 4B
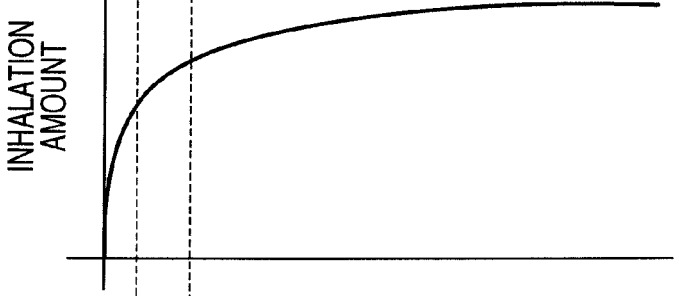
FIG. 4C
FIG. 4D
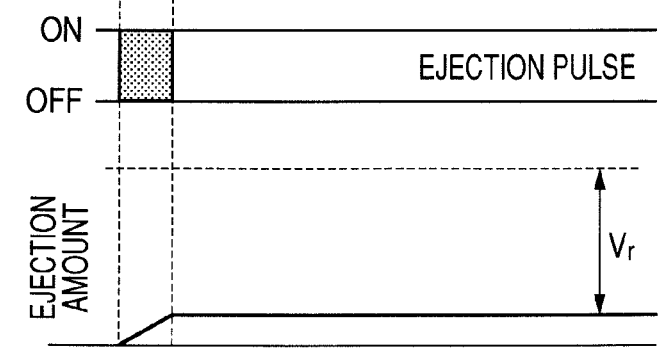

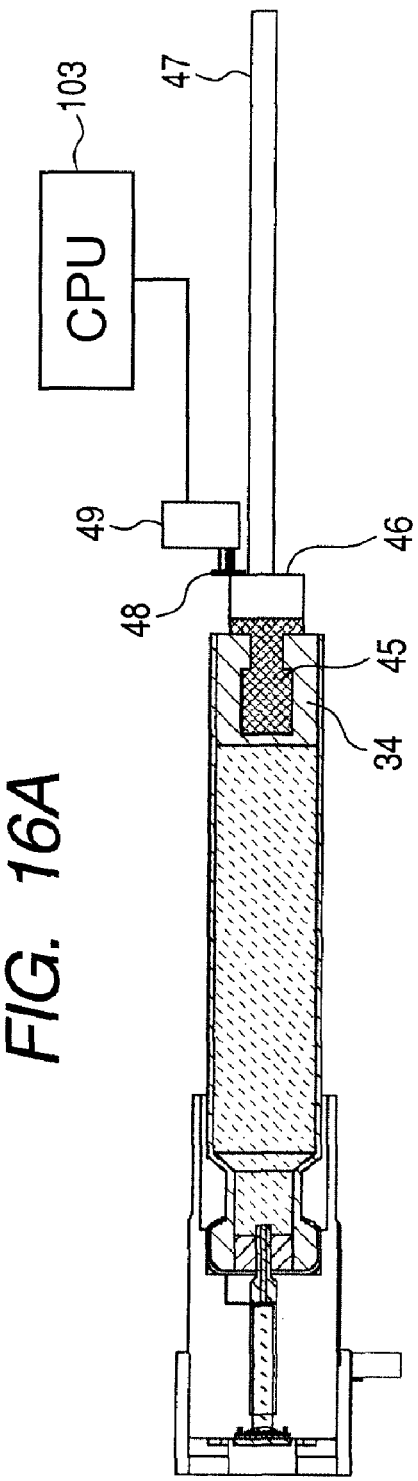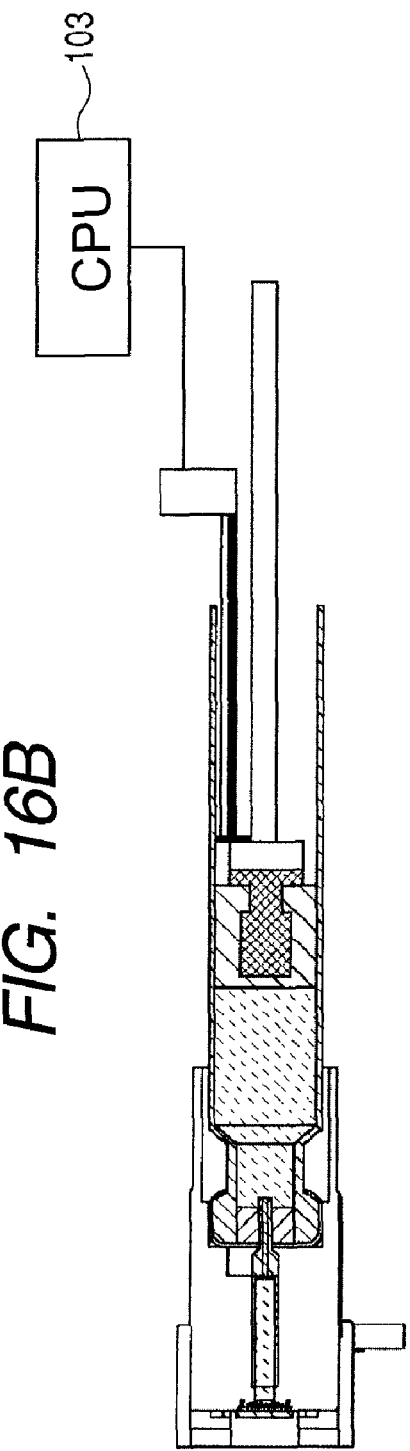
FIG. 16A
FIG. 16B

MEDICINE EJECTION APPARATUS AND CONTROL METHOD THEREOF

TECHNICAL FIELD

The present invention relates to a medicine ejection apparatus which is constructed so that a user can use it and can conveniently carry it, and which can be used for an inhalation apparatus for making the user inhale a medicine, and the like, and its control method.

BACKGROUND ART

In order to deliver a medicine which a medicine ejection apparatus, such as an inhaler, ejects to an objective site effectively, the ejection droplet diameter and the user's respiratory behavior are important factors. For both the ejection droplet diameter and respiratory behavior, there are conditions suitable for each according to the site to which a medicine is to be delivered. Thus, in inhalation treatment, the curative effect is dependent on how the user inhales.

In Japanese Publication of PCT International Application No. H10-507096, it is described that inhalation which has a high lung deposition rate and good efficiency can be achieved by ejecting an aerosolized medicine within a range of determined inhalation flow rate and inhalation amount. The inhalation apparatus disclosed in Japanese Publication of PCT International Application No. H10-507096 can be controlled so as to start ejection of the medicine when the user's inhalation flow rate reaches a predetermined value, and to stop the ejection of the medicine when it reaches a certain predetermined inhalation amount.

In addition, in Japanese Publication of PCT International Application No. 2006-506151, a technique of registering a user's inhalation pattern and spraying in accordance with the pattern is disclosed as a means of causing liquid droplets to be inhaled in a proper inhalation profile. According to this technique, spraying can be synchronized in pulsed manner with breathing by measuring beforehand a user's breathing pattern and recording the information in the inhaler. On the other hand, an inhalation apparatus has been developed, which produces minute liquid droplets of a medicine ejected into an air current path, through which air inhaled through a mouthpiece flows, using the ejection principle of an ink jet system to make a user inhale them (refer to Japanese Patent Application Laid-Open No. 2004-283245). Such inhalation apparatuses have an advantage of being able to spray a predetermined amount of medicine precisely with an equalized particle diameter.

In the inhalation apparatuses described in the above-mentioned background art, even if the inhalation parameters are suitable at the beginning or start of spraying, the subsequent inhalation might not be appropriate. However, it is not expectable that a user inhales precisely the same way each time, and when a medicine is released only while a suitable inhalation profile is achieved, there is no guarantee that the whole dose can be administered by one time of inhalation. For example, when a user stops inhalation for a certain reason in the middle of inhalation, a possibility of an ejection amount of medicine not reaching the dose is high.

Accordingly, in the conventional inhalation apparatuses, it cannot be said that quantitative control can be performed since it is not possible to tell whether the user has inhaled the full dose of the medicine.

DISCLOSURE OF THE INVENTION

An object of the present invention is to provide a medicine ejection apparatus which can medicate a user in a set dose securely regardless of a user's inhalation operation, and its control method, in a medicine ejection apparatus which ejects a medicine according to a user's inhalation behavior.

The present invention is directed to a medicine ejection apparatus which ejects a medicine for medicating a user that comprises a medicine ejecting unit which has an element that generates energy for ejecting the medicine, a drive control unit which controls a drive start and a drive stop of the element, and an ejection amount determining unit which determines a total amount of medicine ejected from the medicine ejecting unit after the element performs a drive stop, the drive control unit enabling the element to perform driving so as to eject an amount of medicine calculated from a difference between the set ejection amount and the total amount of medicine when the total amount of medicine determined by the ejection amount determining unit does not reach the set ejection amount.

The medicine ejection apparatus can comprise a determining unit which determines a driving condition of the element for performing ejection of the amount of medicine calculated from difference between the set ejection amount and the total amount of the medicine.

The medicine ejection apparatus can comprise a sensor for detecting a user's inhalation, and the drive control unit controls a drive start and a drive stop of the element on the basis of an output signal from the sensor.

The medicine ejection apparatus can comprise a display unit that displays the result of determining whether the total amount of medicine determined by the ejection amount determining unit reaches the set ejection amount.

The element can be an electrothermal transducer which imparts heat energy to the medicine.

The ejection amount determining unit can determine the ejection amount on the basis of a driving condition of the electrothermal transducer.

The present invention also is directed to a control method of a medicine ejection apparatus which ejects a medicine for medicating a user, that comprises starting ejection of a medicine, stopping the ejection of the medicine, determining a total amount of the medicine which is ejected from the ejection starting of the medicine to the ejection stop, judging whether the total amount reaches a set ejection amount, and enabling it to eject an amount of medicine calculated from the difference between the set ejection amount and the total amount of the medicine when it is judged that the total amount of the medicine does not reach the set ejection amount.

The control method can comprise determining an ejecting condition for ejecting an amount of medicine calculated from the difference between the set ejection amount and the total amount of the medicine.

The medicine ejection apparatus can start the ejection of the medicine by detecting a user's inhalation and can stop the ejection of the medicine on the basis of the user's subsequent inhalation condition.

According to the medicine ejection apparatus of the present invention, even if an amount of a medicine which is ejected in one inhalation does not reach the ejection amount set beforehand in the apparatus as one dose, the deficient ejection amount (that is, the difference between the amount that should have been ejected and the amount that was ejected) can be ejected. For this reason, a user can be made to inhale the set dose.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 3A, 3B, 3C and 3D are graphs illustrating relation between an ejection period of a medicine and a user's inhalation at the time when a user's inhalation is weak and set ejection amount of the medicine cannot be ejected in one time of inhalation;

FIGS. 4A, 4B, 4C and 4D are graphs illustrating relation between an ejection period of a medicine and a user's inhalation at the time when a user's inhalation rate is excessively strong and it exceeds an upper limit of a suitable inhalation rate;

FIGS. 16A and 16B include sectional views of the medicine cartridge 101 in a third example.

BEST MODES FOR CARRYING OUT THE INVENTION

Figure 1:
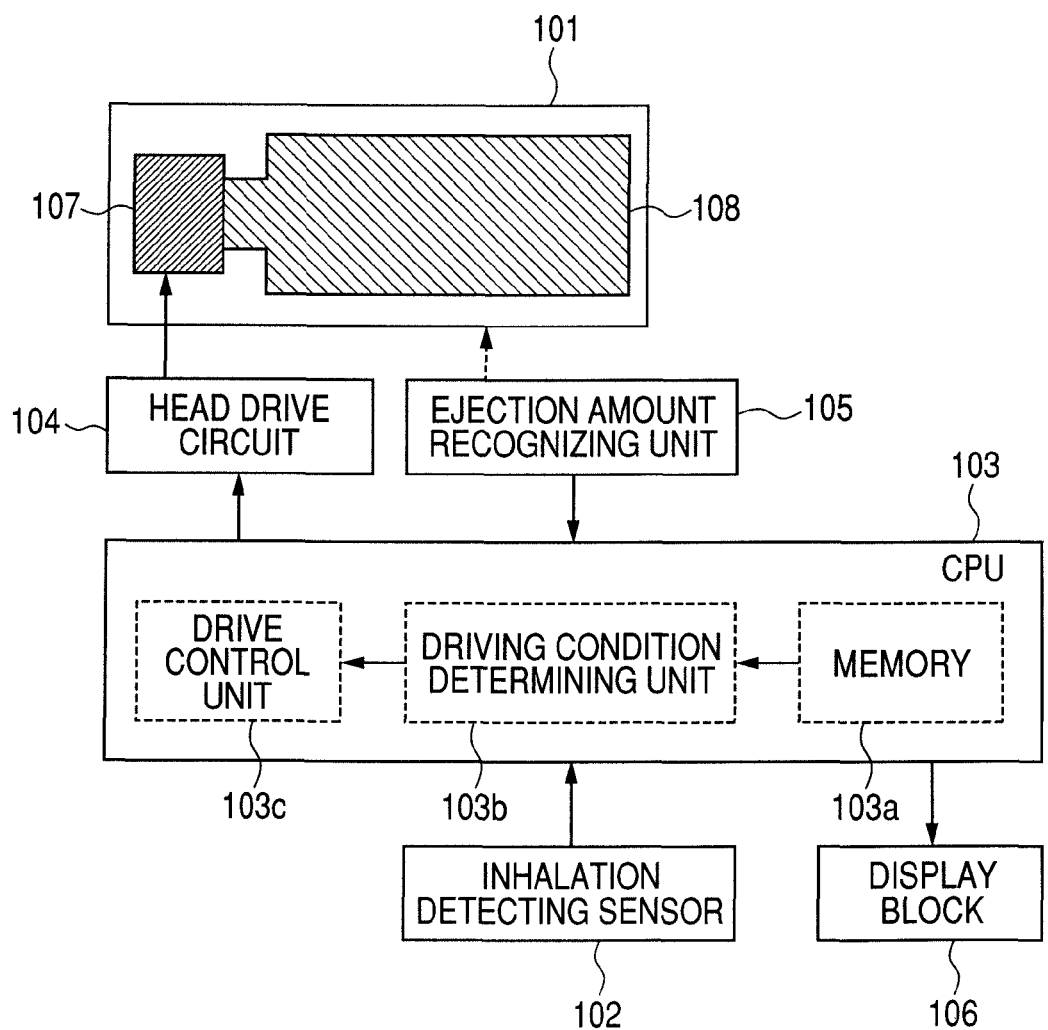
FIG. 1 is a diagram illustrating conceptual construction of a medicine ejection apparatus of the present invention which ejects a medicine for medicating a user.

Preferred embodiments of the present invention will now be described in detail in accordance with the accompanying drawings.

In addition, the same reference numerals are assigned to the same components fundamentally, and their descriptions are omitted.

(Medicine Ejection Apparatus)

A conceptual illustration of the construction of a medicine ejection apparatus of the present invention which ejects a medicine for medicating a user is shown in FIG. 1. An element which generates energy for ejecting the medicine is arranged in the ejection head 107, which is a medicine ejecting unit, and when the element is driven by a head drive circuit 104, the medicine is ejected from an ejection opening. It is suitable that a medicine tank 108 which contains the medicine which is ejected is connected to the ejection head 107, and the ejection head 107 and medicine tank 108 are integrated to form the medicine cartridge 101. Such an integrated type cartridge can be attached to a medicine ejection apparatus detachably. It is suitable that a CPU 103, which is a control unit that controls the whole apparatus, includes at least memory 103a, a driving condition determining unit 103b, and a drive control unit 103c. Many settings of the whole apparatus are stored in the memory 103a, and in particular, a user's dose and the like are stored. Hereinafter, this dose may be called the "set ejection amount." The drive control unit 103c sends a command to the head drive circuit 104 to perform a drive start and a drive stop of an ejection energy generating element, that is, drive control of the ejection head 107. It is a suitable embodiment from a synchronous standpoint of inhalation and ejection that the drive start and drive stop of the element, that is, the control of an ejection start and an ejection stop of a medicine is performed on the basis of an output signal from a sensor 102 which detects a user's inhalation. As in other embodiments, it can be mentioned to start ejection by a user's button operation or the like, and to stop it after performing the ejection for a predetermined time. This specified time can be set at a suitable value beforehand from a user's inhalation time and the like.

When a user's inhalation is detected by the inhalation detecting sensor 102, an output signal is sent to the CPU 103, drive of the ejection head 107 is started by the drive control unit 103c, and the medicine is ejected. In addition, when it determines by the inhalation detecting sensor 102 that a user's inhalation is ended, or when it is determined that it is not in a suitable inhalation state, the drive of the ejection head 107 is stopped by the drive control unit 103c, and the ejection of the medicine is ended. Here, a total amount of the medicine which is ejected in the period of operation is determined by an ejection amount recognizing unit 105, which thus serves as an ejection amount determining unit. Then, it is judged whether the total amount of the ejected medicine reaches the set ejection amount by the total amount of the medicine determined by the ejection amount recognizing unit 105 being compared with the set ejection amount recorded in memory 103a. When it does not reach the set ejection amount, it is enabled again to drive the ejection head 107 by the drive control unit 103c so as to eject an amount of medicine calculated based on the difference from the set ejection amount. Although it is suitable that the calculated amount here is the amount equal to the difference between the set ejection amount and the total amount of the medicine which has been ejected, the present invention is not limited to this. For example, in the case of a medicine which does not need such strict control of the amount administered, such as a steroid, it is also conceivable to administer somewhat more than the above-mentioned difference in the second ejection. An essence of the present invention is to perform the second ejection on the basis of a difference between the ejection amount in the first (or "one-time") ejection, and the ejection amount set beforehand. Even when a dose (set ejection amount) cannot be inhaled by one inhalation, an amount of ejection which is the same as or almost the same as the set ejection amount can be performed.

In this way, when performing the second ejection, it can be performed that the driving condition determining unit 103b as a determining unit determines driving conditions of the ejection head 107 for ejecting the amount of medicine calculated based on the difference from the set ejection amount. Then, according to the determined driving conditions, the apparatus can be operated to eject the same amount (in two ejections) as the set ejection amount by enabling drive of the ejection head 107 by the drive control unit 103c. Even when the ejection amount recognizing unit 105 cannot grasp the ejection amount of medicine in-situ in the midst of ejection, by determining ejection conditions for achieving predetermined ejection amount in advance and performing drive according to the conditions, it can be determined that the ejection of the predetermined amount is completed. In addition, the ejection amount recognizing unit 105 may be arranged in the CPU 103 depending on the embodiment.

Here, second and later ejections may be performed automatically or may be performed by a user's switch depression. When performed automatically, it can be performed on the basis of an output signal from the inhalation detecting sensor 102.

A main body of the medicine ejection apparatus can have a display unit 106, such as an LCD display, and it can be performed to display the determination result showing whether the set ejection amount has been reached, and the like, in this display unit 106.

Here, the medicine ejecting unit (ejection head) 107 has two or more ejection openings, and arbitrary ejection energy generating elements provided in relation of one-to-one, one-to-many and many-to-one to an ejection opening. An electrothermal transducer which imparts heat energy to the medicine, or an electromechanical transducer which imparts mechanical energy, can be mentioned as examples. That is, as the ejection methods of a medicine, a method (thermal jet system) of giving heat energy to a medicine and making it ejected using an electrothermal transducer, and a method (piezo-jet system) of ejecting a medicine using oscillating pressure of an electromechanical transducer (for example, a piezoelectric element) which gives mechanical energy to the medicine can be exemplified. These systems may be called ink jet systems. The ejection method is selectable according to the type of medicine being administered, or the like.

When a thermal jet system is used, it can be performed to enhance size accuracy and repeatability of an aperture of an ejection opening, heat amount of a thermal pulse used for ejection, and a micro heater as an electrothermal transducer, in regard to each ejection head. Thus, it can be performed to achieve a narrow droplet diameter distribution. In addition, head manufacturing cost is low and applicability to small apparatuses which need frequent exchange of a head is also high. Hence, when the medicine ejection apparatus is requested to have portability or convenience, in particular, an ejection principle of a thermal jet type can be adopted.

Here, a determination method of the driving conditions for controlling ejection amount of a medicine arbitrarily will be exemplified. First, the ejection amount is changeable by changing an ejecting operation period when the medicine is ejected. Here, in this specification, the "ejecting operation period" or "ejection period" means the time from giving a first pulse to the ejection energy generating element to finishing the application of the last pulse of a continuously applied series of pulses, that is, a series of period while a pulse train for ejection energy generation is supplied. It can be performed to increase the medicine ejection amount by making the ejecting operation period longer. In addition, it can be also performed to change ejection amount by changing the ejection frequency of the ejection energy generating element instead of changing the ejecting operation period. Here, the "ejection frequency" is equivalent to the number of pulse signals for ejecting the medicine given to the ejection energy generating element per unit time. This may be called a drive frequency.

In addition, the ejection amount of the medicine for achieving a necessary dosage may be changed by combining these both methods.

As an inhalation detecting sensor used for the present invention, a pressure sensor arranged in an air current path can be exemplified. It can be operated to grasp inhalation conditions, such as a user's inhalation start and subsequent inhalation strength, by the pressure sensor detecting a pressure change (negative pressure fluctuation) generated in the air current path by a user's inhalation. Besides that, a common flow rate sensor which measures a gas flow rate in the air flow path can be used.

The term "medicine" used in the present disclosure includes not only a medicine such as a pharmaceutical compound which shows a pharmacological and physiological effect, but also a component for providing a seductive taste or a seductive smell, a dye, a pigment, and the like in addition to pharmaceutical compounds. It does not matter whether a medicine is liquid or powder.

In addition, the "medical fluid" used for the present invention encompasses a liquid medicine or a liquid medium including a medicine. Arbitrary additive agents may be included in the medical fluid. Any of a dissolution, dispersion, emulsification, suspension, and slurry may be sufficient as a state of the medicine in liquid, and when equalized in liquid, it is better.

When using a medical liquid as a medicine, it is suitable that the main medium of the liquid is plain water or an organic solvent, and in consideration of being administered into a living body, it is suitable that plain water is the main medium.

(Operation Pattern)

One time of ejecting operation period of the medicine ejection apparatus which is a suitable embodiment of the present invention and has the inhalation detecting sensor 102 depends on a user's inhalation condition. In such a case, in particular, total amount of the medicine which is ejected in one time of ejecting operation period may not reach ejection amount set beforehand as one dose. A control method of the medicine ejection apparatus of the present invention which can eject set ejection amount securely also in such a case although inhalation is divided into multiple times will be specifically described below.

Figure 2A:
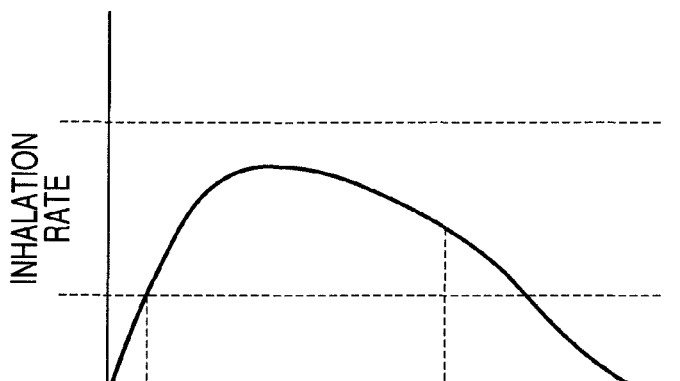
FIGS. 2A, 2B, 2C and 2D are graphs illustrating relation between an ejection period of a medicine and a user's inhalation at the time when a user performs suitable inhalation.
Figure 2B:
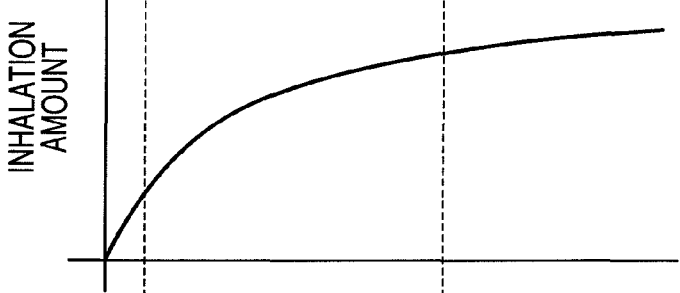
Figure 2C:
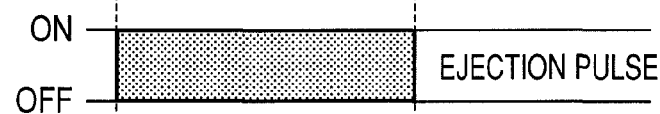
Figure 2D:
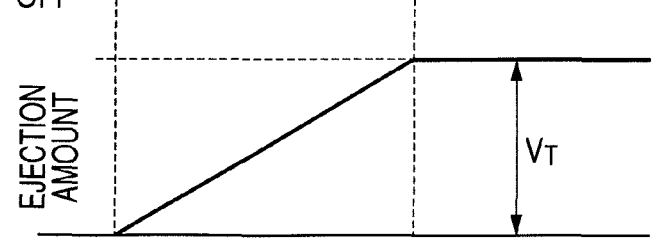
Figure 5:
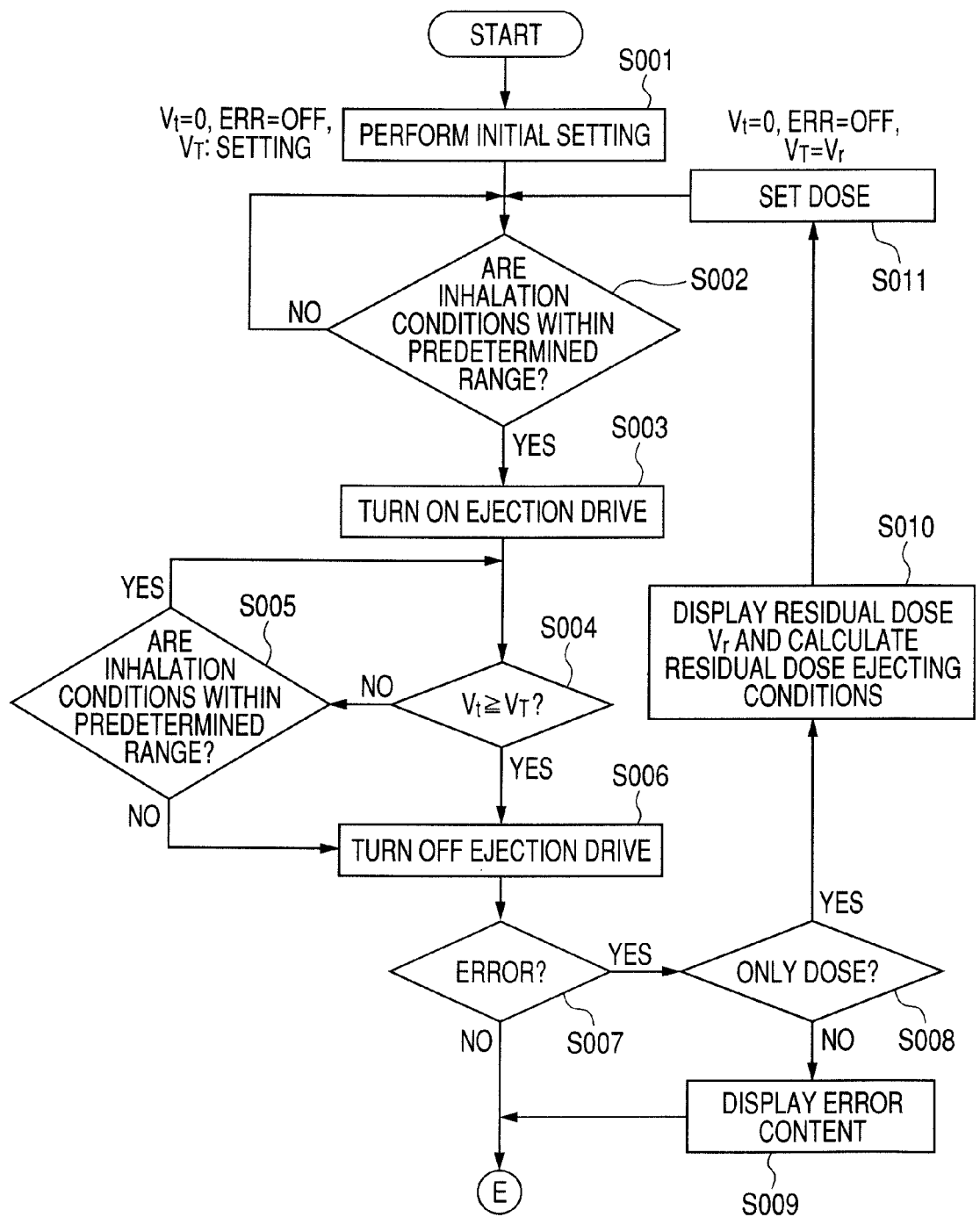
FIG. 5 is a chart illustrating an example of a control method of the medicine ejection apparatus of the present invention in a flowchart.

Patterns considered as a relation between the medicine ejection period and the user's inhalation are illustrated in FIGS. 2A to 4D. FIGS. 2A, 3A, and 4A illustrate changes of user's inhalation rate (inhalation strength) which is measurable directly by an inhalation detecting sensor. These are also called "inhalation profiles." FIGS. 2B, 3B and 4B are the time series changes of the inhalation amount from an inhalation start, and become time integration values of inhalation profiles which are illustrated in FIGS. 2A, 3A, and 4A, respectively. FIGS. 2C, 3C, and 4C illustrate periods when a pulse is given to an ejection energy generating element. A period illustrated by shading is an ejection period. FIGS. 2D, 3D, and 4D illustrate the ejection total amount of the medicine in each time. The horizontal axis is the time in each case.

FIGS. 2A to 2D illustrate cases where a user performs suitable inhalation. Ejection of a medicine is performed only within the range of the user's inhalation flow rate being in the predetermined inhalation flow rate illustrated by dotted lines in FIG. 2A. Ejection is started by the drive control unit 103c when a user starts inhalation and predetermined inhalation flow rate is detected. Ejection is ended when it reaches set ejection amount $V_T$ without stopping ejection while inhalation flow rate is kept within a suitable range. In this case, the set ejection amount can be ejected in one time of inhalation.

FIGS. 3A to 3D are graphs of cases where a user's inhalation is weak and the set ejection amount cannot be ejected in one inhalation. Since the inhalation rate falls below the lower limit of the predetermined range before the set amount is ejected, ejection is stopped. The total amount $V_t$ of the medicine which is ejected is determined by the ejection amount recognizing unit 105, and a residual dose $V_r$ ($=V_T-V_t$) is ejected at the time of the next inhalation. Driving conditions of the element for it are determined by the driving condition determining unit 103b.

Even when ejection is performed according to the determined driving conditions at the time of second inhalation, since ejection is performed only within the proper range described above, it is conceivable that it may not reach the set ejection amount even in the second inhalation. In that case, the total amount of the medicine which has been ejected again is calculated, and the amount resulting from adding the total amount of the medicine which was ejected at the time of the first inhalation, and the set ejection amount are compared. Then, driving conditions are determined again so as to eject the amount of medicine corresponding to difference from the set ejection amount. This operation is repeated until the total amount of the medicine which is ejected reaches the set ejection amount.

FIGS. 4A to 4D are graphs illustrating cases where a user's inhalation rate is too strong and exceeds an upper limit of a proper inhalation rate. Even though the user's inhalation rate falls to within the proper limits and ejection is started, the ejection is stopped because of the upper limit being exceeded. After that, although it enters the proper limits once again in a second half of the inhalation operation, it can be performed not to eject the medicine in the meantime. This is because it is clear that lung deposition efficiency falls in the second half of inhalation since the user's one-time inhalation amount is already close to saturation. Similarly to the case of FIGS. 3A to 3D, difference between the total amount of the medicine which is ejected and the set ejection amount is calculated and a user is prompted to perform next inhalation. Then, similarly, in accordance with the inhalation, ejection is performed until it reaches the set ejection amount.

Although a suitable inhalation rate range is approximately 0.1 to 1.0 L/s or so for an adult, it may change with individual difference, illness, conditions, and the like.

As respiratory parameters used for the inhalation conditions which determine the ejection period, besides the above-mentioned inhalation rate, inhalation amount may be used. The term "inhalation rate" means speed of an air current generated in an air current path, and is calculated on the basis of speed of air which passes a given point in an inhalation detection unit. The "inhalation amount" is the amount of inhaled air, which is calculated by time integration of inhalation rate data.

Suitable inhalation conditions differ according to the medicine to be used. According to a site of the respiratory organ in which the medicine is made to act, a suitable droplet diameter, a particle size distribution, and inhalation conditions which are suitable for them are set.

If a medicine to be inhaled is a bronchodilator, it is better for it not to arrive at the pulmonary alveoli, since the intended site to be acted on is the bronchi. Although optimum conditions also depend on a user's physical and physiological features, it turns out that generally it is better to achieve proper delivery of the medicine by controlling the liquid droplets' particle size distribution, and not to increase inhalation flow rate and inhalation amount.

In addition, in the case of whole body dosing as with insulin, it is better to avoid deposition in the bronchi, and to make the liquid droplets arrive at the pulmonary alveoli. Also, at this time, although optimum conditions also depend on a user's physical and physiological features, it turns out that generally it is better to cause the diameter of the liquid droplets be 1 to 5 μm, make the particle size distribution sharp, make the inhalation rate small, and increase the inhalation amount.

Setting of an inhalation condition is set so that an ejection flag (FLG) may become ON when an inhalation rate is within a certain range. Furthermore, it is also good to find the inhalation amount from time integration of an inhalation rate and to add a rate with a user's maximum inspiratory capacity (IC), which was measured beforehand, to the condition. By adding the inhalation amount on the condition, it can be performed to deliver a spraying medicine to lungs before the lungs are filled with air to be inhaled.

It is desirable that the setting of actual inhalation conditions is determined on the basis of a medicine used and an analysis of a user's respiratory profile. Data of a general pulmonary function test is used for the analysis of a respiratory profile, and the inhalation conditions are set. Such inhalation condition data may be recorded on a recording medium inside a main body of the inhaler, or a user may store it in external memory.

(Flowchart of Apparatus Drive)

An example of a control method of the medicine ejection apparatus of the present invention is illustrated in a flowchart in FIG. 5. First, when a power source of an apparatus is turned on by a user pushing a power button or the like, the medicine ejection apparatus performs initial setting (S001). Specifically, it is confirmed whether the set ejection amount $V_T$ is set as one dose in the memory 103*a*, and count of the ejection total amount $V_t$ at the time t from an ejection start is reset to zero. In addition, error detection is reset. The CPU 103 monitors an output signal from the inhalation detecting sensor 102, and confirms whether inhalation conditions fall in the predetermined ranges (S002). When a user starts inhalation and the inhalation conditions fall in the predetermined ranges, drive of the ejection head 107 is started by the drive control unit 103*c*, and ejection of a medicine is started (S003). When the inhalation conditions do not fall in the predetermined ranges, ejection start is deferred until they are suitable.

It is determined during ejection whether or not the ejection amount $V_t$ of the medicine achieved as yet has reached the set ejection amount $V_T$ (S004). A method of performing this determination will be exemplified below.

First, the ejection amount $V_t$ can be determined in-situ by the ejection amount recognizing unit 105. In this case, whether the set ejection amount $V_T$ is reached can be determined directly. Next, since the ejection conditions for ejecting the set ejection amount $V_T$ are determined, it may be determined by whether or not ejection on the ejection conditions has been completed.

When $V_t$ reaches $V_T$ by this determination, the ejection is ended (S006). During ejection, it is also continuously monitored whether the inhalation conditions fall in the predetermined range on the basis of the output signal of the inhalation detecting sensor 102 (S005). When the inhalation conditions fall in the predetermined range, the ejection is continued. When the inhalation conditions move out of the predetermined range, the ejection is ended even if the amount ejected has not reached $V_T$ (S006). When the ejection is ended, error determination is performed (S007). Here, not only determination of whether the ejection amount has reached $V_T$ but determination of, for example, whether temperature and resistance of a minute heater as the ejection energy generating element indicate unusual values and the ejection has been not normally performed are performed. When there is no error, the power source is turned OFF as what the predetermined amount of ejection has been completed, and the operation is ended. When there is an error, processing shifts to a decision step, discussed below (S008). When there is an error other than an error in the ejection amount (N), the error contents are shown on a display block 106, and the user is warned of them (S009). In the case of an error in the ejection amount, the residual dose $V_r (=V_T-V_t)$ is shown, and the user is prompted to perform a second inhalation. In addition, the ejection conditions at the time of ejecting the $V_r$ are calculated according to necessity by the driving condition determining unit 103b (S010). A counter that monitors the ejection amount $V_t$ is reset to zero, and the set ejection amount $V_T$ in the second ejection is replaced temporarily with the residual ejection amount $V_r$. Error detection is reset (S011). The above-mentioned flow is repeated hereafter until the set ejection amount is ejected completely.

(Ejection Amount Recognizing Unit)

As means for determining ejection amount used for the present invention, it can be calculated from the number of given pulses (hereafter, this is called an ejection shot number) and a droplet diameter when an ejection principle of an ink jet is used for a medicine ejecting unit. Since it is dependent on the diameter of an ejection opening (nozzle), the droplet diameter can be grasped as a constant beforehand and an ejection shot number can be calculated from ejection conditions. In this calculation method, even if ejection is performed with ejection conditions being changed during one inhalation, its ejection amount can be grasped accurately.

In addition, when the volume of the medicine tank 108 changes according to the amount of a medicine inside, the amount which is ejected can be also grasped by detecting the volume change. As for the volume change, a method of detecting a displacement of a movable wall, which forms a part of the medicine tank 108, by a distance sensor such as an optical type, or an ultrasonic type, can be mentioned. In addition, since a liquid amount supplied to the ejection head 107 can be measured by installing a liquid flow rate sensor between the ejection head 107 and the medicine tank 108, ejection amount can be also grasped from this value.

Furthermore, in the case where the medicine tank 108 is an airtight container isolated from the open air apart from the ejection opening of the ejection head 107 and it is not necessary to change the volume of the medicine tank during ejection, the ejection amount can be also grasped by measuring a pressure change occurring in the medicine tank corresponding to ejection amount. For example, a pressure sensor which measures internal pressure of the medicine tank can be used.

These ejection amount recognizing units may be used independently, or may be used in combination.

Example 1

Figure 6:
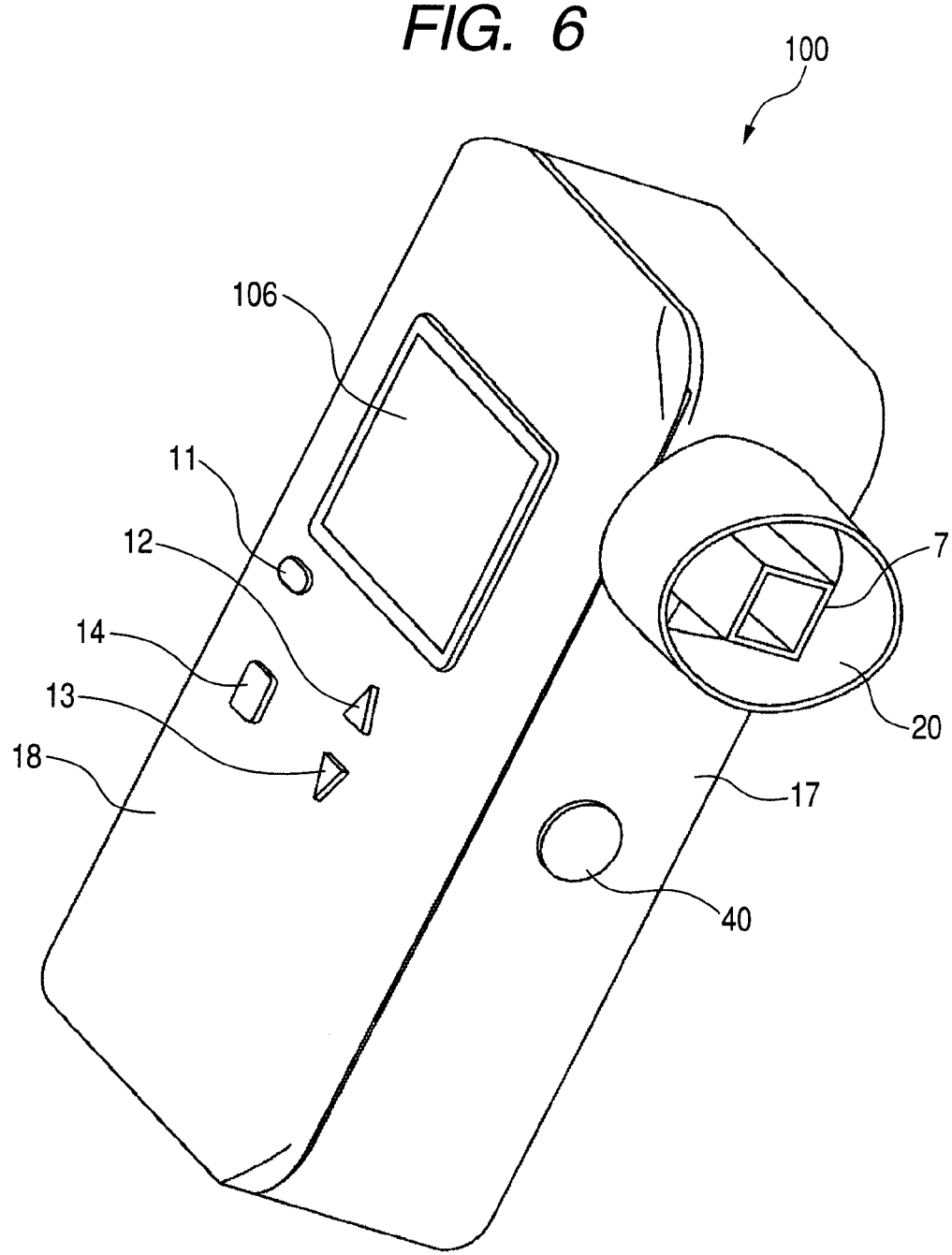
FIG. 6 is a perspective view illustrating appearance of an inhaler 100 which is an example of the medicine ejection apparatus of the present invention and makes a user inhale a medicine.

FIG. 6 is a perspective view illustrating the appearance of an inhaler 100 which is an example of the medicine ejection apparatus of the present invention and makes a user inhale a medicine. The main body is formed by a housing case 17 and an access cover 18. Reference numeral 40 denotes a lock release button of the access cover. To ensure that the access cover 18 does not open in use, a hook portion 19 (FIG. 7) is provided and is caught by a hook holding shaft which operates integrally with a lock release button 40 energized by a spring. This is constructed so that, when the access cover 18 is opened, a catch of the hook may be released by the release button 40 being pushed and the access cover 18 is pushed toward an open position by a (not illustrated) spring. The display unit 106 for displaying a dose, time, an error, and the like is provided in the access cover 18. In addition, a menu switching button 11 for a user to perform setting, an up button 12 and a down button 13 which are setting buttons, and a determination button 14 are provided.

Figure 7:
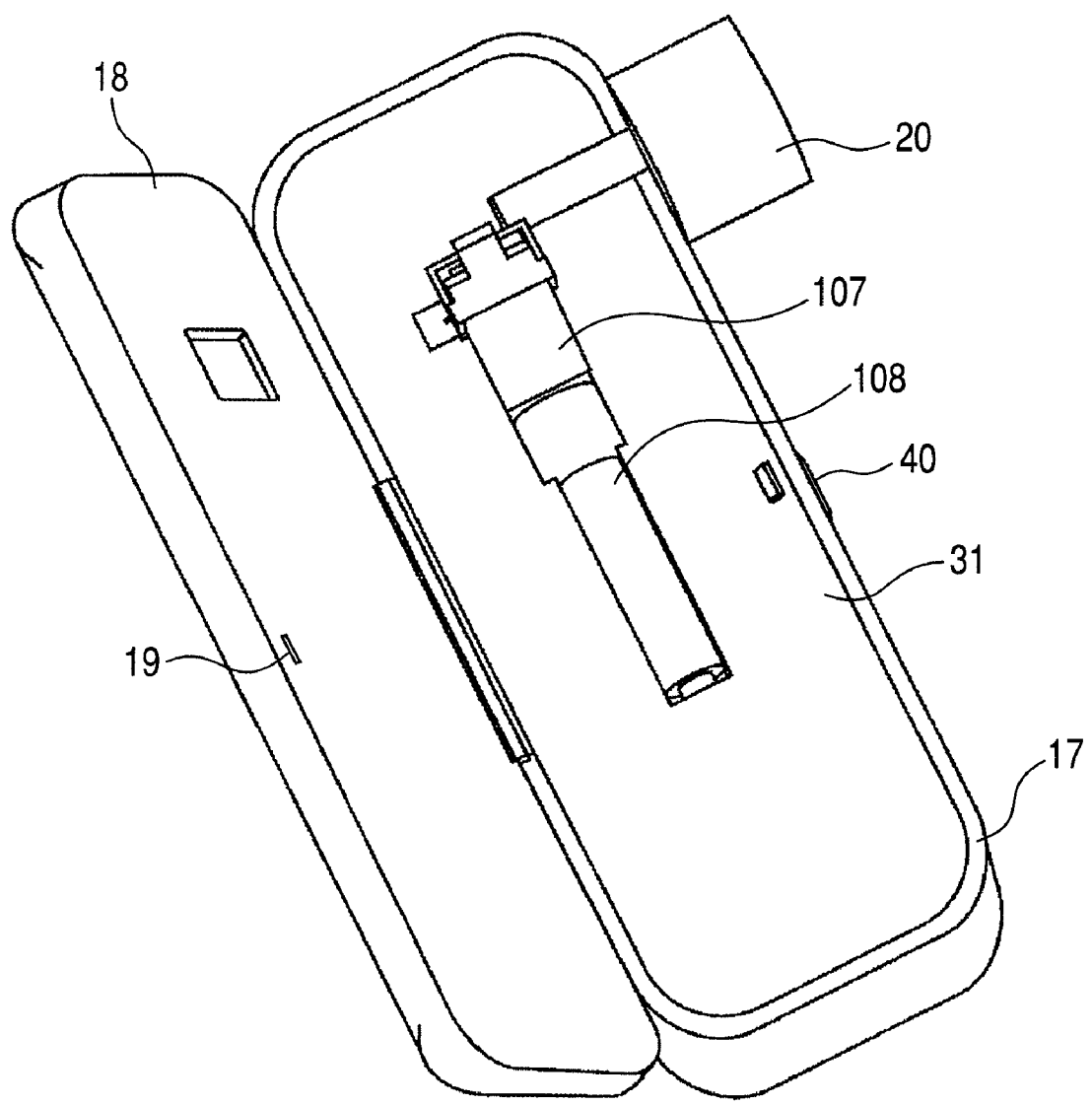
FIG. 7 illustrates a state where an access cover 18 is open in the inhaler in FIG. 6.

FIG. 7 illustrates a state in which the access cover 18 is open in the inhaler in FIG. 6. When the access cover 18 opens, the ejection head unit 107, which is a medicine ejecting unit that is detachable from the apparatus body, and the medicine tank 108, which is a medicine containing unit, can be seen. The ejection head unit 107 ejects the medicine toward an air current path 7. Although the air current path 7 is illustrated in FIG. 6, its part is hidden by a cover 31 in FIG. 7. By inhaling a breath from an inlet (mouthpiece) 20, a user can inhale the medicine which is ejected into the air current path 7. In this embodiment, the inlet 20 and air current path 7 are integrated. The inlet 20 is thrown away after use and replaced, or it is washed after inhalation and is re-used. The ejection head unit 107 and the medicine tank 108 will be exchanged when the amount of a medicine in the medicine tank 108 becomes less than the set ejection amount $V_T$. For example, since a function of counting ejection amount is performed in the main body and the residual amount is computable by this ejection amount count function, it is feasible to perform notification of exchange time to prompt a user to exchange the head unit 107 and tank 108, or not to perform ejection until exchange is completed. Reference numeral 31 denotes a drive unit protective cover that keeps the user from touching the internal mechanism of the inhaler easily. In the back of the drive unit protective cover 31, an electric board on which a CPU 103, ROM, RAM, and the like which are arranged inside the apparatus body, and various control circuits are mounted, drive mechanisms, such as a motor, detection units, such as a sensor, a battery, and the like are settled.

Figure 8:
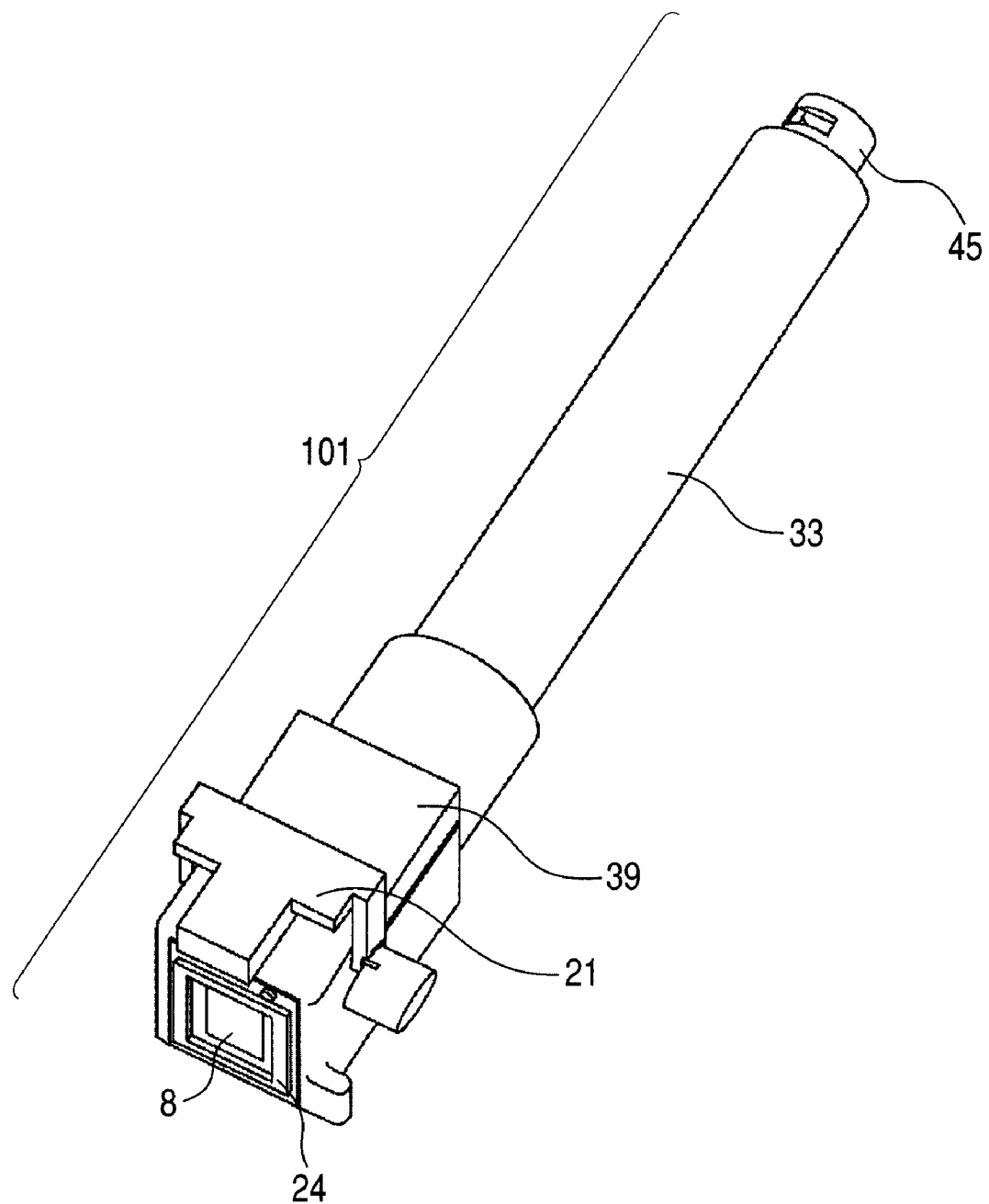
FIG. 8 is a drawing illustrating a perspective view of a cartridge 101 that an ejection head unit 107 and a medicine tank 108 are integrated.

A perspective view of the cartridge 101 into which the ejection head unit 107 and medicine tank 108 are integrated is illustrated in FIG. 8. The head protective cap 21 has a medical fluid absorber so as to contact an ejection opening surface of the ejection head 8 for the purpose of preventing the ejection opening from being deformed or being stained. The head protective cap 21 releases the ejection head 8 so as to allow ejection of the medicine from the ejection opening to the air current path 7 at the time of medicine ejection. A release state is illustrated in FIG. 8.

The ejection head unit 107 is mainly constructed of a housing 39, and the ejection head 8 is a thermal ink jet type ejection head publicly known in the field of ink jet printers. There is a frame 24, which the cap 21 contacts at the time of protection and which is made of rubber, in the periphery of the ejection opening surface of the ejection head 8. An electrical connection member (contact pin) for supplying electric power for making a heater provided in the ejection head 8 generate heat energy from a power source provided in the main body is arranged on a (not illustrated) surface of the housing 39.

Figure 9:
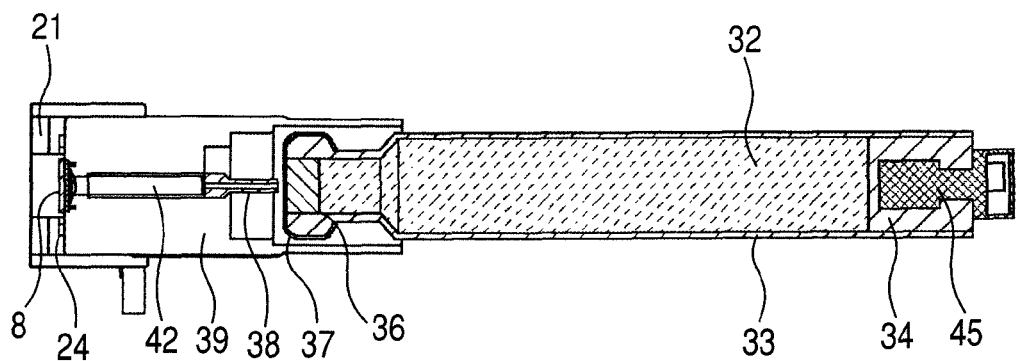
FIG. 9 is a principal sectional view in a state where a cap 21 protects an ejection head 8 in FIG. 8.

FIG. 9 is a principal sectional view showing a state in which the cap 21 protects the ejection head 8 in FIG. 8. Inside the housing 39, there is a hollow needle 38, with a medical fluid pass 42 connected thereto, and a medical fluid is supplied to the ejection head 8. The medicine tank 108 is mainly constructed of a glass container 33 for accommodating a medicine. At a tip of the glass container 33, a fixed rubber stopper 36 is held down by the glass container 33 with a caulking or sealing metal fitting 37 which is made of aluminum. Then, in a rear edge side of the glass container 33, a movable rubber stopper 34 is provided; the movable rubber stopper 34 moves as a result of the amount of medicine 32 decreasing due to ejection from the inhaler. The required sealing property of the medicament container 33 is maintained by this construction, and denaturation and concentration change of the medicine 32 are suppressed to the minimum. In the movable rubber stopper 34, a connection joint 45 with a main body side plunger for moving this positively is provided.

Figure 10:
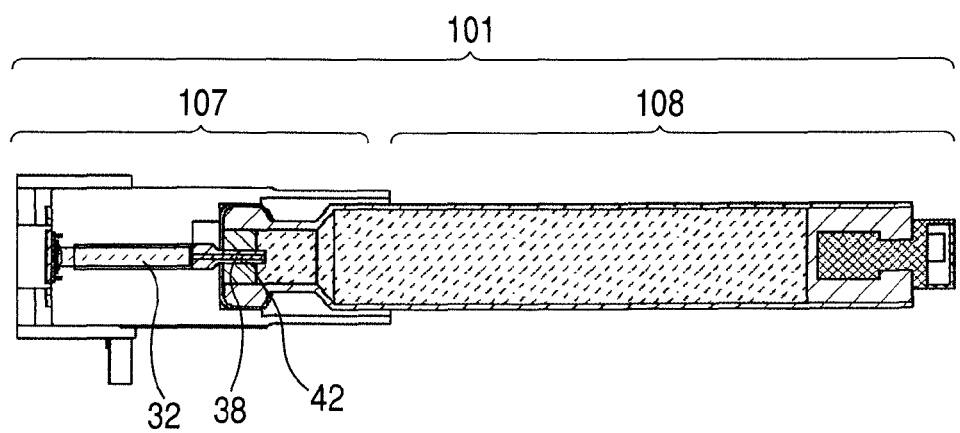
FIG. 10 is a sectional view in a state where the medicine tank 108 is pushed into the ejection head unit 107 in FIG. 9, and both are made to communicate.

FIG. 10 is a sectional view showing a state in which the medicine tank 108 is pushed into the ejection head unit 107 in FIG. 9, and the two are made to communicate. It illustrates the point in time at which the hollow needle 38 breaks through the fixed rubber stopper 36, a medicine pass 42 is formed, and the medicine in the medicine tank 108 flows into the ejection head 8. Ejection is enabled by the medicine being filled in a heater, a top face portion and an ejection nozzle of the ejection head unit. Filling of the medicine 32 (FIG. 11) into the ejection head 8 is performed by pushing the movable rubber stopper 34.

In the above construction, a method by calculation from the number of ejected liquid droplets can be used as a means of determining and grasping the ejection amount. Formula 1 is an operational expression of ejection amount on the basis of digital ejection by an ink jet system:

$$V_t = V_1 \times n \times f \times t \times A \quad \text{(Formula 1)}$$

$V_t$: Amount ejected after t seconds
$V_1$: Volume of one liquid droplet
n: Number of nozzles
f: Ejection frequency
t: Ejection drive time
A: Correction Value Here, the correction value A is a coefficient which corrects volume by liquid droplets called satellites (which are droplets other than the main liquid droplets) ejected from one nozzle when one drive pulse is applied. In an ink jet system, since an ejected droplet's diameter is dependent on the diameter of a nozzle, the particle diameter of the main liquid droplets is constant. In addition, it can be performed to measure the amount ejected in t seconds accurately by recording values of $V_1$ and A beforehand, since ejection of satellites also is constant given a set of ejection conditions. It is considered that the ejection of the satellites is affected by, for example, pulse width and the drive voltage. "Pulse width" here is application time in one pulse signal application. In addition, the "drive voltage" is a voltage applied to an ejection energy generating element. Since the nozzle number n is the number of holes ejecting a medicine, the number used for ejection is inserted into Formula 1. The nozzle number to be used is changeable with the ejection conditions.

Figure 11:
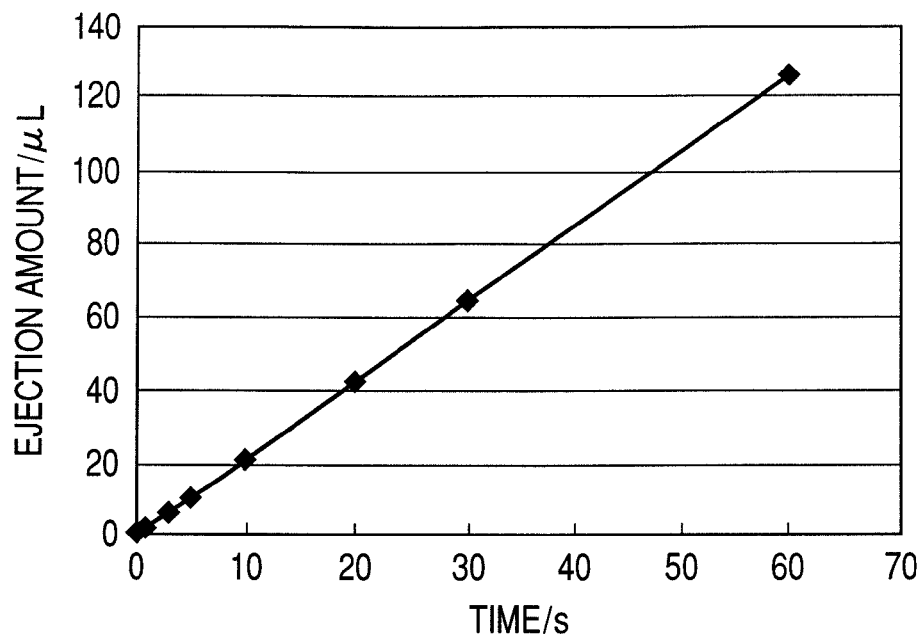
FIG. 11 is a drawing illustrating relation between an ejecting operation period and ejection amount in a graph.

The relation between the ejecting operation period and the ejection amount is illustrated in a graph in FIG. 11. An experiment of ejecting de-ionized water with an ejection frequency of 10 kHz, a droplet diameter of 5.6 μm, and a nozzle number of 2000 was conducted, and the ejection amount in plotted respective ejection periods was measured. The ejection amount was determined by using a thin pipe (inner diameter: 1.6 mmϕ) for liquid supply to an ejection head, measuring the length of the column of liquid ejected, and calculating the volume ejected from them. The ejection amount results were almost proportional to the ejecting operation period. When these experimental conditions are applied to Formula 1:

$$V_t = 4/3 \cdot \Pi \cdot (2.8)^3 \times 2000(\text{nozzles}) \times 10(\text{kHz}) \times t(\text{seconds}) \times 1.15 \quad (1)$$

This well coincided with the result in FIG. 11.

Figure 12:
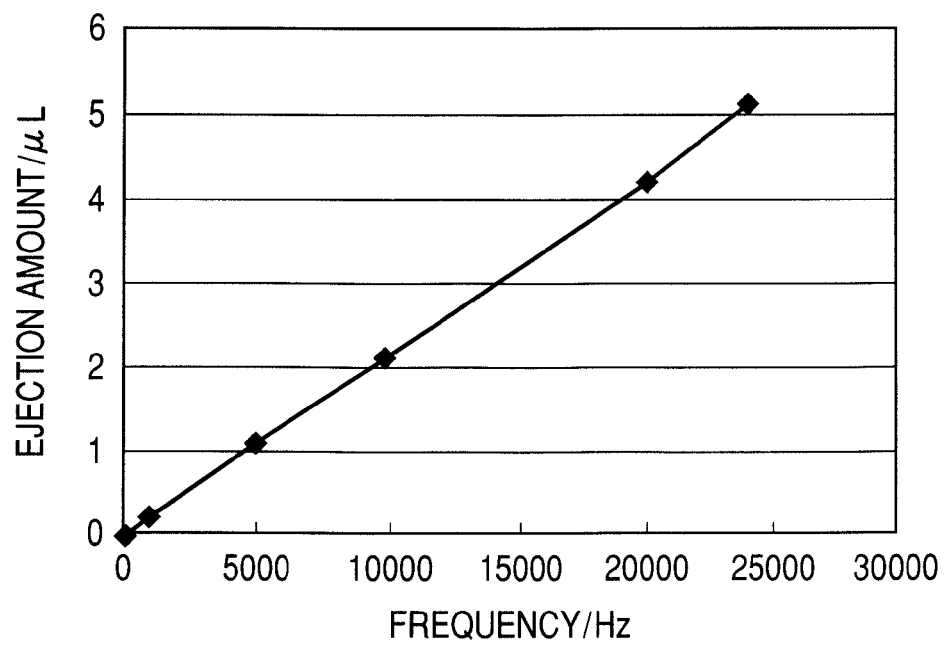
FIG. 12 is a drawing illustrating relation between an ejection frequency and ejection amount in a graph.

The relation between the ejection frequency and the ejection amount is illustrated in a graph in FIG. 12. An experiment of ejecting de-ionized water with an ejection time of 1.0 second, a droplet diameter of 5.6 μm, and a nozzle number of 2000 was conducted, and the ejection amount at respective ejection frequencies was measured. The ejection amount results were almost proportional to the ejection frequency. When these experimental conditions are applied to Formula 1 similarly:

$$V_t = 4/3 \cdot \Pi \cdot (2.8)^3 \times 2000(\text{nozzles}) \times f(\text{kHz}) \times 1.0(\text{second}) \times 1.15 \quad (2)$$

This well coincided with the result in FIG. 12.

In this way, when the ejection principle of an ink jet system is used, the ejection total amount in a predetermined ejection period can be calculated from the ejection conditions. If residual ejection amount $V_r$ is calculated, the ejection conditions of the second ejection are determined, but when not changing the conditions, such as an ejection frequency, the driving condition determining unit 103b determines so as to shorten the ejection period as compared with in the first ejection. In this way, when this embodiment is adopted, it is necessary to determine the ejection conditions in the second ejection.

When a range of a suitable inhalation rate is 0.1 to 1.0 L/s and detection is performed with a pressure sensor in an air current path portion in a sectional area of 10 mm², the above-mentioned suitable range is detectable as −0.12 to −6 kPa.

Example 2

Figure 13:
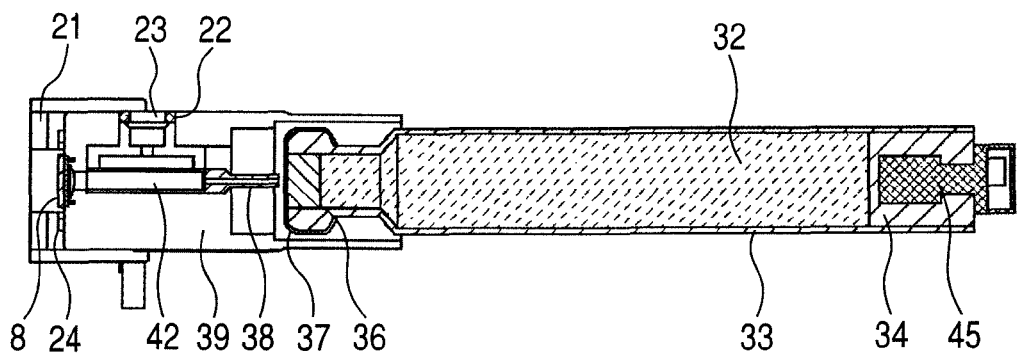
FIG. 13 is a sectional view before connection of the medicine cartridge 101 in a second example.
Figure 14:
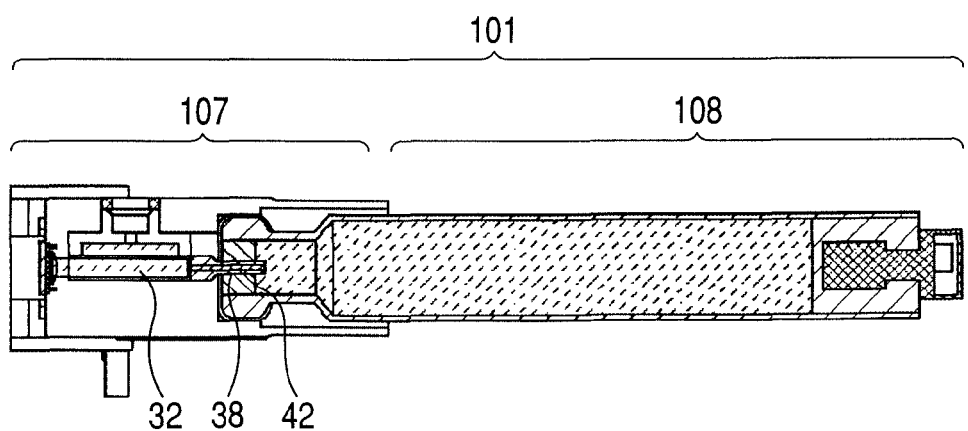
FIG. 14 is a sectional view after the connection of the medicine cartridge 101 in the second example.

Next, an embodiment of a method of determining ejection amount from an internal pressure change of a medicine tank will be described. Although the outline of the main body of the inhalation apparatus is the same as in the first example, in this embodiment, it has a construction in which the medicine cartridge 101 can measure pressure in the medicine tank 108. Sectional views of the medicine cartridge 101 in this embodiment are illustrated in FIGS. 13 and 14. FIG. 13 shows that before connection and FIG. 14 shows that after the connection.

Inside the ejection head unit 107, there are the hollow needle 38 and the medical fluid pass 42 connected thereto, and a medical fluid is supplied to the ejection head 8. The medical fluid pass 42 branches in the direction of a pressure detection opening 23 on the way. A pressure sensor provided in a side of the inhalation apparatus body is connected to the pressure detection opening 23. In the pressure detection opening 23, a sealant (O-ring) 22 for preventing a pressure leak at the time of the pressure sensor connection after main body attachment is arranged.

Pressure in the tank is transmitted from a branched small hole to the pressure detection opening 23 through a space in an upper portion. The upper portion (a surface dividing the pressure detection opening 23 and this space) of this space becomes a membrane which is constructed from a flexible material, and detects a tank internal pressure from a displacement of the membrane by a pressure change by the pressure sensor in the side of the main body. The other main features of construction of the medicine cartridge 101 are the same as in the first example.

Figure 15:
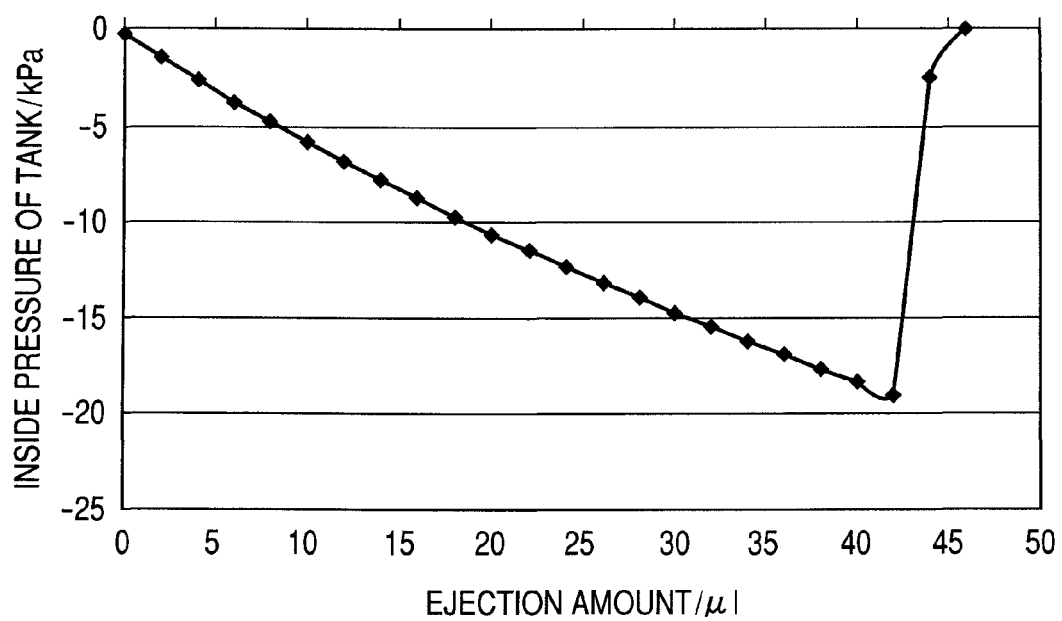
FIG. 15 is a drawing illustrating experimental result of investigating relation between pressure and ejection amount in the medicine tank 108 in a graph.

Experimental results of investigating relation between the pressure and the ejection amount in the medicine tank 108 are illustrated in a graph in FIG. 15. Ejection was performed with a tank internal volume of 2 mL, a droplet diameter of 3 μm, ejection frequency 10 kHz, and one-second ejection, and an ejection amount of 2 μL/time. During the ejection, the movable rubber stopper 34 is fixed so as not to move. In addition, the interior of the medicine tank 108 is an airtight container, and it is isolated from the open air apart from the ejection opening of the ejection head 8. Therefore, when the medical fluid is ejected from the ejection opening 8, corresponding to the ejection amount, negative pressure occurs in the container. As long as the negative pressure was small, the negative pressure value and the ejection amount were in almost proportional relation, but when the ejection amount declined little by little and became near −20 kPa as the negative pressure became large, air was drawn from the ejection head, and ejection could not be performed. Under these conditions, the ejection amount can be determined to the extent of 40 μl by this method.

Hence, so long as the above-mentioned relation between the tank internal pressures and the ejection amount is beforehand stored in the inhalation apparatus body, the ejection amount can be determined Example 3

Sectional views of the medicine cartridge 101 according to the third embodiment of the present invention are illustrated in FIGS. 16A and 16B. FIG. 16A is a sectional view showing an early stage of ejection, and 16B is one showing a state in which ejection is advancing and the medical fluid in the medicine tank is decreasing. In this embodiment, the movable rubber stopper 34 is moved by a piston while keeping the negative pressure in the medicine tank constant during ejection. In this case, since movement amount of the rubber stopper and the ejection amount of the medical fluid correspond in one-to-one relation, the ejection amount can be determined by measuring the movement of the rubber stopper.

Since an iron core 45 is fixed to the movable rubber stopper 34 and a magnet 46 provided at a tip of a plunger 47 attracts mutually with the iron core 45 with a magnetic force, the plunger 47 and movable rubber stopper 34 are fixed. According to the ejection of the medical fluid, the movable rubber stopper 34 is moved by the plunger 47.

A position sensor 49 is provided opposite to the movable rubber stopper 34, and a detection plate 48 is provided in a part of the magnets 46. The ejection amount can be measured accurately by reading the movement amount of the movable rubber stopper 34 using the position sensor 49.

Hence, so long as the relation between the movement amount of the rubber stopper and the ejection amount is beforehand stored in the inhalation apparatus body, the ejection amount can be determined The medicine ejection apparatus of the present invention may be used for various uses besides for medicine inhalation. For example, it can be also used for a spray form ejecting apparatus of aromatics, an inhalation apparatus of luxury goods, such as nicotine, and the like. Thus, the medicine ejection apparatus of the present invention is applicable to various uses which need certain and sanitary ejection.

The present invention is not limited to the above embodiments and various changes and modifications can be made within the spirit and scope of the present invention. Therefore to apprise the public of the scope of the present invention, the following claims are made.

This disclosure is submitted in a national-phase entry of International Application PCT/JP2009/051515, and claims the benefit of Japanese Patent Applications No. 2008-014458, filed Jan. 25, 2008, and No. 2008-103554, filed Apr. 11, 2008, which are hereby incorporated by reference herein in their entirety.

The invention claimed is:

1. A medicine ejection apparatus which ejects a medicine for medicating a user, comprising:
   a medicine tank equipped with a movable stopper, said medicine tank containing the medicine;
   a position sensor which measures a movement amount of said movable stopper;
   a medicine ejecting unit which has an element that generates energy for ejecting the medicine from said medicine ejection apparatus;
   a drive control unit which controls a drive start and a drive stop of said element; and
   an ejection amount determining unit which determines a total amount of the medicine that has been ejected from the medicine ejecting unit, based on the movement amount measured by said position sensor, after said element has performed a drive stop,
   wherein said drive control unit enables said element to perform driving so as to eject an additional amount of the medicine calculated from a difference between the set ejection amount and the total amount of the ejected medicine when the total amount of the ejected medicine determined by said ejection amount determining unit is less than the set ejection amount.

2. The medicine ejection apparatus according to claim 1, further comprising a determining unit which determines a driving condition of said element for performing ejection of the amount of medicine calculated from the difference between the set ejection amount and the total amount of the medicine that has been ejected.

3. The medicine ejection apparatus according to claim 1, further comprising a sensor for detecting a user's inhalation, and wherein said drive control unit controls a drive start and a drive stop of said element on the basis of an output signal from said sensor.

4. The medicine ejection apparatus according to claim 1, further comprising a display unit which displays a result of determining whether the total amount of the medicine determined by said ejection amount determining unit reaches the set ejection amount.

5. The medicine ejection apparatus according to claim 1, wherein said element is an electrothermal transducer which imparts heat energy to the medicine.

6. The medicine ejection apparatus according to claim 5, wherein said ejection amount determining unit determines ejection amount on the basis of a driving condition of said electrothermal transducer.

7. A control method of a medicine ejection apparatus which ejects a medicine for medicating a user, comprising:
   generating energy for ejecting a medicine from a medicine ejection apparatus;
   starting an ejection of the medicine and stopping the ejection of the medicine using the energy generated by the generating;
   measuring a movement amount of a movable stopper included in a medicine tank containing the medicine;
   determining a total amount of the medicine that has been ejected from the starting of the ejection to the stopping of the ejection based on the measuring;
   judging whether the total amount equals a set ejection amount; and
   ejecting an additional amount of the medicine calculated from a difference between the set ejection amount and the total amount of the medicine that has been ejected when the total amount of the medicine that has been ejected is judged to be less than the set ejection amount.

8. The control method according to claim 7, further comprising determining an ejecting condition for ejecting an amount of medicine calculated from the difference between the set ejection amount and the total amount of the medicine that has been ejected.

9. The control method according to claim 7, wherein the medicine ejection apparatus starts the ejection of the medicine by detecting a user's inhalation and stops the ejection of the medicine on the basis of the user's subsequent inhalation condition.

* * * * *